(12) United States Patent
Jupe et al.

(10) Patent No.: US 6,355,427 B1
(45) Date of Patent: Mar. 12, 2002

(54) DIAGNOSTIC ASSAY FOR BREAST CANCER SUSCEPTIBILITY

(75) Inventors: Eldon R. Jupe, Norman; Linda F. Thompson, Oklahoma City, both of OK (US); Regina Resta, Slingersland, NY (US); Robert T. Dell'Orco, Gaithersburg, MD (US)

(73) Assignee: Oklahoma Medical Research Foundation, Oklahoma City, OK (US)

( * ) Notice: Subject to any disclaimer, the term of this patent is extended or adjusted under 35 U.S.C. 154(b) by 0 days.

(21) Appl. No.: 09/297,911

(22) PCT Filed: Nov. 6, 1997

(86) PCT No.: PCT/US97/20844

§ 371 Date: May 7, 1999

§ 102(e) Date: May 7, 1999

(87) PCT Pub. No.: WO98/20167

PCT Pub. Date: May 14, 1998

Related U.S. Application Data

(60) Provisional application No. 60/029,978, filed on Nov. 7, 1996.

(51) Int. Cl.[7] ................................................. C12Q 1/68
(52) U.S. Cl. ............................................................ 435/6
(58) Field of Search .................................... 435/6, 91.2

(56) References Cited

U.S. PATENT DOCUMENTS

| 5,401,635 A | 3/1995 | Nakamura et al. ............. 435/6 |
| 5,776,738 A * | 7/1998 | Dell'Orco et al. ........... 43/91.2 |

FOREIGN PATENT DOCUMENTS

| WO | WO9640919 | 12/1996 |

OTHER PUBLICATIONS

Jupe, et al. 1996. "The 3' untranslated region of prohibitin and cellular immortalization," *Experimental Cell Research* 224: 128–135.

Jupe, et al. 1996. "Prohibitin in breast cancer cell lines: loss of antiproliferative activity is linked to 3' untranslated region mutations," *Cell Growth & Differentiation* vol. 7, 871–878.

Jupe, et al. 1995. "Prohibitin antiproliferative activity and lack of heterozygosity in immortalized cell lines," *Experimental Cell Research* 218: 577–580.

Sato, et al. 1992. "The human prohibitin gene located on chromosome 17q21 is mutated in sporadic breast cancer," *Cancer Research* 52 :1643–1646.

Bentley, et al 1991. "Rapid methods for detection of polymorphic markers in genomic DNA," *Methods in Molecular Biology* vol. 9: Protocols in Human Molecular Genetics pp. 51–68.

Liu, et al. 1995. "Restriction endonuclease fingerprinting (REF): a sensitive method for screening mutations in long, contiguous segments of DNA," *BioTechniques* vol. 18: 470–477.

* cited by examiner

Primary Examiner—Eggerton A. Campbell
(74) Attorney, Agent, or Firm—Fitch, Even, Tabin & Flannery

(57) ABSTRACT

The lifetime probability of a woman developing breast cancer can now be determined based on an allelic variation found in the 3'UTR of the prohibitin gene. The probability is dependent on the sequence of the 3'UTR at position 729, i.e., whether there is a thymine (T) or a cytosine (C) or both at this position. Polymorphism at position 729 is also disclosed as a susceptibility indicator for hereditary breast cancer in men. Determining the sequence at the position 729 can be done by any number of standard techniques. Preferably, the sequence is determined by amplifying this region by PCR and subjecting it to an RFLP analysis.

41 Claims, 5 Drawing Sheets

FIG. 1A

|         | 680        | 690        | 700        | 710        | 720         | 730        | 740       |
|---------|------------|------------|------------|------------|-------------|------------|-----------|
| WT   5'-| AGTGGAATTC | CAACTTGAAG | GATTGCATCC | TGCTGGGGCT | ..GAACATGCCT | GCCAAAGACG | TGTCCGACCT |
| TN-56 (T) | AGTGGAATTC | CAACTTGAAG | GATTGCATCC | TGCaGGGGCT | ..GAACATGCCT | GCCAAAGATG | TGTCCGACCT |
| (N)       | AGTGGAATTC | CAACTTGAAG | GATTGCATCC | TGCTGGGGCT | ..GAACATGCCT | GCCAAAGACG | TGTCCGACCT |
| TN-78 (T) | AGTGGAATTC | CAACTTGAAG | GATTGCATCC | TGCaGGGGCT | ..GAACATGCCT | GCCAAAGATG | TGTaCatCCT |
| (N)       | AGTGGAATTC | CAACTTGAAG | GATTGCATCC | TGCTGGGGCT | ..GAACATGCCT | GCCAAAGACG | TGTCCGACCT |
| TN-50 (T) | AGTGGAATTC | CAACTTGAAG | GATTGCATCC | TGCTGGGGCT | ..GAACATGCCT | GCCAAAGATG | TGTtGACCT |
| (N)       | AGTGGAATTC | CAACTTGAAG | GATTGCATCC | TGCTGGGGCT | ..GAACATGCCT | GCCAAAGACG | TGTCCGACCT |
| SK-BR-3   | AGTGGAATTC | CAACTTGAAG | tATTGaATCC | TtCTGGGGCT | ..aAACATGCCT | GCCAAAGATG | TGTaCatCCT |
| TN-1 (T)  | gGaataAATTC | CAAgcTtgAa | tgTccaATCC | TtCTGGGGtT | tctAAagatCCT | GCCAAAGATG | TGTaCatCCT |
| (N)       | AGTGGAATTC | CAACTTGAAG | GATTGCATCC | TGCTGGGGCT | ..GAACATGCCT | GCCAAAGACG | TGTCCGACCT |
| TN-3 (T)  | AaTGGAATTC | CAACTTGAAG | tATTGaATCC | TtCT--GGCT | ..aAACATGCCT | GCCAAAGACG | TGTaCatCCT |
| (N)       | AGTGGAATTC | CAACTTGAAG | GATTGCATCC | TGCTGGGGCT | ..GAACATGCCT | GCCAAAGACG | TGTCCGACCT |
| TN-31 (T) | AaTGGAATTC | CAACTTGAAG | tATTGaATCC | TtCTGGGGCT | ..aAACATGCCT | GCCAAAGATG | TGTaCatCCT |
| (N)       | AGTGGAATTC | CAACTTGAAG | GATTGCATCC | TGCTGGGGCT | ..GAACATGCCT | GCCAAAGACG | TGTCCGACCT |
| TN-94 (T) | AaTGGAATTC | CttCTTGAAG | tATTGaATCC | TtCTGGGGCT | ..aAACATGCCT | GCCAAAGACG | TGTaCatCCT |
| (N)       | AGTGGAATTC | CAACTTGAAG | GATTGCATCC | TGCTGGGGCT | ..GAACATGCCT | GCCAAAGACG | TGTCCGACCT |

|  | 750 | 760 | 770 | 780 | 790 | 800 |
|---|---|---|---|---|---|---|
| WT | ACGTTCCTGG CCCCCTCGTT | CAGAGACTGC | CCTTCTCACG | GGCTCTATGC | CTGCACTGGG | AAGGAAACAA-3' |
| TN-56 (T) | ACGTTCCTGG CCCCCTCGTT | CAGAGACTGC | CCTTCTCACG | GGCTCTATGC | CTGCACTGGG | AAGGAAACAA |
| (N) | ACGTTCCTGG CCCCCTCGTT | CAGAGACTGC | CCTTCTCACG | GGCTCTATGC | CTGCACTGGG | AAGGAAACAA |
| TN-78 (T) | ACGTTCCTGG CCCCCTCGTT | CAGAGACTGC | CCTTCTCACG | GGCTCTATGC | CTGCACTGGG | AAGGAAACAA |
| (N) | ACGTTCCTGG CCCCCTCGTT | CAGAGACTGC | CCTTCTCACG | GGCTCTATGC | CTGCACTGGG | AAGGAAACAA |
| TN-50 (T) | ACGTTCCTGG CCCCCTCGTT | CAGAGACTGC | CCTTCTCACG | GGCTCTATGC | CTGCACTGGG | AAGGAAACAA |
| (N) | ACGTTCCTGG CCCCCTCGTT | CAGAGACTGC | CCTTCTCACG | GGCTCTATGC | CTGCACTGGG | AAGGAAACAA |
| SK-BR-3 | gtGTTCCTGG CttCCTtgTT | CAGAGACTGC | tCTTCTCcaG | GGCTCTgTGC | CTGtgCTttG | A---AAAcAg |
| TN-1 (T) | gtGTTCCTGG CttCCTtgTT | CgagaACgaC | tCTTCTCcac | GGCTCTgTGC | CTGtgCTttG | AAGGAAACAA |
| (N) | ACGTTCCTGG CCCCCTCGTT | CAGAGACTGC | CCTTCTCACG | GGCTCTATGC | CTGCACTGGG | AAGGAAACAA |
| TN-3 (T) | gtGTTCCTGG CttCCTtgTT | CAGAGACTGC | tCTTCTCcaG | GGCTCTgTGC | CTG---TGca | AAGaAAAtAg |
| (N) | ACGTTCCTGG CCCCCTCGTT | CAGAGACTGC | CCTTCTCACG | GGCTCTATGC | CTGCACTGGG | AAGGAAACAA |
| TN-31 (T) | gtGTTCCTGG CttCCTtgTT | CAGAGACTGC | tCTTCTCcaG | GGCTCTgTGC | CTGtgCTttG | A---AAAtAg |
| (N) | ACGTTCCTGG CCCCCTCGTT | CAGAGACTGC | CCTTCTCACG | GGCTCTATGC | CTGCACTGGG | AAGGAAACAA |
| TN-94 (T) | gtGTTCCTGG CttCCTtgTT | CAGAGACTGC | tCTTgTCcaG | GGCTCTgTGC | CTGtggTttG | AAGGAAACAA |
| (N) | ACGTTCCTGG CCCCCTCGTT | CAGAGACTGC | CCTTCTCACG | GGCTCTATGC | CTGCACTGGG | AAGGAAACAA |

FIG. 1B

```
  1  CCCAGAAATC ACTGTGAAAT TTCATGATTG GCTTAAAGTG AAGGAAATAA
     ─────────────────────
             P1
 51  AGGTAAAATC ACTTCAGATC TCTAATTAGT CTATCAAATG AAACTCTTTC
101  ATTCTTCTCA CATCCATCTA CTTTTTTATC CACCTCCCTA CCAAAAATTG
151  CCAAGTGCCT ATGCAAACCA GCTTAGGTC CCAATTCGGG GCCTGCTGGA
201  GTTCCGGCCT GGGCACCAGC ATTTGGCAGC ACGCAGGCGG GGCAGTATGT
251  GATGGACTGG GGAGCACAGG TGTCTGCCTA GATCCACGTG TGGCCTCCGT
301  CCTGTCACTG ATGGAAGGTT TGCGGATGAG GGCATGTGCG GCTGAACTGA
351  GAAGGCAGGC CTCCGTCTTC CCAGCGGTTC CTGTGCAGAT GCTGCTGAAG
401  AGAGGTGCCG GGGAGGGGCA GAGAGGAAGT GGTCTGTCTG TTACCATAAG
451  TCTGATTCTC TTTAACTGTG TGACCAGCGG AAACAGGTGT GTGTGAACTG
501  GGCACAGATT GAAGAATCTG CCCCTGTTGA GGTGGGTGGG CCTGACTGTT
551  GCCCCCAGG GTCCTAAAAC TTGGATGGAC TTGTATAGTG AGAGAGGAGG
                                ──────────────────
                                        P4
601  CCTGGACCGA GATGTGAGTC CTGTTGAAGA CTTCCTCTCT ACCCCCCACC
                          ──────────────────────
                                  P3
651  TTGGTCCCTC TCAGATACCC AGTGGAATTC CAACTTGAAG GATTGCATCC
701  TGCTGGGGCT GAACATGCCT GCCAAAGACG TGTCCGACCT ACGTTCCTGG
751  CCCCCTCGTT CAGAGACTGC CCTTCTCACG GGCTCTATGC CTGCACTGGG
801  AAGGAAACAA ATGTGTATAA ACTGCTGTCA ATAAATGACA CCCAGACCTT
                                           ──────────────────
                                                   P2
851  CC
     ──
```

FIG. 2

```
   1  AGGACTGGTG GGCAATGTGC TCTGCTTCCC CCCGCTTCCC CCGCTAGCCA
  51  TCAGGAGGAA GTAAACTCCC CGAGTTCCTT CAGGAGCCTG GGAAGGTGGC
 101  TTTCTGGTGA AGGGCCTTTG GTTGTAGCCT GACATGCGGT GCCCTGAGGT
           P1'
 151  TTGATCTTTG TCTCCACCTC CATTCTTTTA GGCTGAGCAA CAGAAAAAGG
 201  CGGCCATCAT CTCTGCTGAG GCGACTCCA  AGGCAGCTGA GCTGATTGCC
 251  AACTCACTGG CCACTGCAGG GGATGGCCTG ATCGAGCTGC GCAAGCTGGA
 301  AGCTGCAGAG GACATCGCGT ACCAGCTCTC ACGCTCTCGG AACATCACCT
 351  ACCTGCCAGC GGGGCAGTCC GTGCTCCTCC AGCTGCCCCA GTGAGGGCCC
 401  ACCCTGCCTG CACCTCCGCG GGCTGACTGG GCCACAGCCC CGATGATTCT
 451  TAACACAGCC TTCCTTCTGC TCCCACCCCA GAAATCACTG TGAAATTTCA   24
                                      *
 501  TGATTGGCTT AAAGTGAAGG AAATAAAGGT AAAATCACTT CAGATCTCTA   74
 551  ATTAGTCTAT CAAATGAAAC TCTTTCATTC TTCTCACATC CATCTACTTT  124
 601  TTTATCCACC TCCCTACCAA AAATTGCCAA GTGCCTATGC AAACCAGCTT  174
 651  TAGGTCCCAA TTCGGGGCCT GCTGGAGTTC CGGCCTGGGC ACCAGCATTT  224
 701  GGCAGCACGC AGGCGGGGCA GTATGTGATG GACTGGGGAG CACAGGTGTC  274
 751  TGCCTAGATC CACGTGTGGC CTCCGTCCTG TCACTGATGG AAGGTTTGCG  324
                      ++++++           P3'
 801  GATGAGGGCA TGTGCGGCTG AACTGAGAAG GCAGGCCTCC GTCTTCCCAG  374
 851  CGGTTCCTGT GCAGATGCTG CTGAAGAGAG GTGCCGGGGA GGGGCAGAGA  424
 901  GGAAGTGGTC TGTCTGTTAC CATAAGTCTG ATTCTCTTTA ACTGTGTGAC  474
 951  CAGCGGAAAC AGGTGTGTGT GAACTGGGCA CAGATTGAAG AATCTGCCCC  524
1001  TGTTGAGGTG GGTGGGCCTG ACTGTTGCCC CCAGGGTCC  TAAAACTTGG  574
1051  ATGGACTTGT ATAGTGAGAG AGGAGGCCTG GACCGAGATG TGAGTCCTGT  624
1101  TGAAGACTTC CTCTCTACCC CCCACCTTGG TCCCTCTCAG ATACCCAGTG  674
1151  GAATTCCAAC TTGAAGGATT GCATCCTGCT GGGGCTGAAC ATGCCTGCCA  724
                                               P4'
1201  AAGACGTGTC CGACCTACGT TCCTGGCCCC CTCGTTCAGA GACTGCCCTT  774
      ******
1251  CTCACGGGCT CTATGCCTGC ACTGGGAAGG AAACAAATGT GTATAAACTG  824
1301  CTGTCAATAA ATGACACCCA GACCTTCC                         852
              P2
```

FIG. 3

DIAGNOSTIC ASSAY FOR BREAST CANCER SUSCEPTIBILITY

This Application is a 371 of PCT/US97/20844, filed on Nov. 6, 1997 and claims benefit of 60/029,978 filed on Nov. 7, 1996.

TECHNICAL FIELD OF THE INVENTION

The invention relates to a diagnostic assay for determining susceptibility to breast cancer based on the sequence of the 3' untranslated region of the prohibitin gene.

BACKGROUND OF THE INVENTION

Breast cancer is the second leading cause of cancer-related deaths of women in North America. A distinction must be drawn, however, between sporadic and familial or inherited breast cancer. Approximately 10% of all breast cancers are currently classified as strongly familial with many of these appearing to be caused by mutations in the hereditary breast cancer genes BRCA1 or BRCA2. However, at least one-third of breast cancers which seem to run in families are not linked to BRCA1 or BRCA2, suggesting the existence of an additional hereditary breast cancer gene or genes. Recently, studies have suggested the possibility that additional genes important for breast cancer development are located on chromosome 17, based on the observation of tumor suppression in breast cancer cells following the introduction of normal human chromosome 17 without the inclusion of active BRCA1 or p53 (Theile, et al., "Suppression of tumorigenicity of breast cancer cells by transfer of human chromosome 17 does not require transferred BRCA1 and p53 genes," *Oncogene* 10:439–443 (1995)).

The antiproliferative gene prohibitin was discovered using a subtraction hybridization to enrich for mRNAs preferentially expressed in normally proliferating cells compared to regenerating rat liver cells (McClung, et al., "Isolation of a cDNA that hybrid selects antiproliferative mRNA from rat liver," *Biochem Biophys Res Comm* 164:1316–1322 (1989); Nuell, et al., "Prohibitin, an evolutionarily conserved intracellular protein that blocks DNA synthesis in normal fibroblasts and HeLa cells," *Mol Cell Biol* 11:1372–1381 (1991)). The human prohibitin gene, which maps to chromosome 17 at q21 (White, et al., "Assignment of the human prohibitin gene (PHB) to chromosome 17 and identification of a DNA polymorphism," *Genomics* 11:228–230 (1991)), was an initial candidate gene for the familial breast and ovarian tumor suppressor locus based on a frequent loss of heterozygosity in this region in familial and sporadic breast cancers (Black, et al., "A somatic cell hybrid map of the long arm of human chromosome 17, containing the familial breast cancer locus (BRCA1)," *Am J Hum Genet* 52:702–710 (1993); Nagai, et al., "Detailed deletion mapping of chromosome segment 17q12–21 in sporadic breast tumors," *Genes, Chromosome and Cancer* 11:58–62 (1994)). Furthermore, Sato, et al., "The human prohibitin gene located on chromosome 17q21 is mutated in sporadic breast cancer," *Cancer Res* 52:1643–1646 (1992), reported four mutations in a highly conserved region of prohibitin exon 4 in an analysis of 23 sporadic human breast cancers. However, positional cloning studies resulted in the identification of BRCA1 rather than prohibitin (Miki, et al., "A strong candidate for the breast and ovarian cancer susceptibility gene BRCA1," *Science* 266:66–71 (1994)) as a familial breast cancer gene on chromosome 17.

Previous studies of the prohibitin gene from DNA purified from familial breast cancer patients provided no evidence that any of the patients carried a germline change of the protein coding region of prohibitin genomic DNA. It was therefore concluded that there was no relationship between familial/hereditary breast cancer and mutations in the prohibitin protein coding region. Tokino, et al., *Internat'l J Oncol* 3:769–772 (1993). Additional studies did not identify any somatic mutations in the prohibitin protein coding region in familial/hereditary breast cancers suggesting that the protein coding region is not frequently mutated in breast cancers. Sato et al., *Genomics* 17:762–764 (1993).

Previous work by Jupe et al. disclosed a diagnostic test for increased susceptibility to sporadic breast cancer. It was reported that individuals who are heterozygous for the two prohibitin alleles (designated as "non-B" and "B" based on sequence variations found in intron 2 and 5) or homozygous for non-B allele would have low risk for developing sporadic cancer. The probability of developing cancer would increase for those who are homozygous for the B-type allele and again for those who have a mutation in the 3' untranslated region ("3'UTR") of at least one of the B-type alleles. Analyses were reported of breast-cancer derived cell lines and primary breast tumors showing homozygosity for the B-type allele and somatic mutations in the 3'UTR.

Full length prohibitin cDNAs for the BT-20, MCF7 and SK-BR-3 breast cancer cell lines were sequenced, and mutations restricted to the 3'UTR were identified. These three cell lines were arrested in cell cycle progression when full length prohibitin transcript was introduced by microinjection. All of them were also homozygous for the B-allele. Compared to the sequence of the wild type prohibitin 3'UTR, two point mutations were identified for BT-20: G (guanine) to A (adenine) at position 758 and T (thymine) to C (cytosine) at position 814. MCF7 also had two point mutations: G to A at position 236 and C to T at position 729. SK-BR-3 showed 26 base changes including a change of C to T at position 729. Thus, MCF7 and SK-BR-3 both had a change of C to T at position 729. Jupe, et al., "Prohibitin in breast cancer cell lines: Loss of antiproliferative activity is linked to 3' untranslated region mutations," *Cell Growth and Differentiation* 7:871–878 (1996).

It has now been found, contrary to the teachings of the prior prohibitin work, that this change from C to T at position 729 is the result not of a somatic mutation, but rather the result of a natural allelic variation at this point, i.e., it is a germline polymorphism. Furthermore, it is a germline polymorphism that can be used as a susceptibility marker for breast cancer. Data indicate that the frequency of homozygosity for 729-T appears to be approximately 4–5-fold higher in breast cancer patients than in unaffected females, that 4% of all breast cancers develop in women who are homozygous T/T (which likely make up less than 1% of unaffected women), and that their lifetime risk of developing breast cancer is approximately 50%.

Thus, it has now been found that the prohibitin gene, located on chromosome 17q21 near the BRCA1 locus, exhibits a germline polymorphism in the 3'UTR that can be used as a susceptibility marker for breast cancer.

BRIEF DESCRIPTION OF THE DRAWINGS

FIG. 1A and FIG. 1B show the alignment of mutated prohibitin 3'UTR sequences obtained from micro-dissected patient tumors. The figures show the sense DNA strand of a frequently mutated 140 bp stretch located at the 3' end of the 3'UTR, with the first 70 bases given in FIG. 1A and the last 70 bases given in FIG. 1B. The sequences of the two wild-type (WT) alleles which differ only at position 729 are shown at the top. The mutated sequences from seven different patient (TN-X) breast tumors (T) are aligned with the sequences obtained from adjacent normal (N) tissue. These adjacent normal sequences were all identical except at position 729. This position contained either a C or T (C/T). The sequence from the heavily mutated breast cancer cell line, SK-BR-3 is shown in the center of the figures. The small case letters depict base changes relative to the wild type sequence. Insertions are shown by additional small case letters and deletions are depicted by dashes. The variant base at UTR-729 is enclosed in the shaded box and the six base AflIII recognition site is enclosed in the large box.

FIG. 2 illustrates the 5'-3' sense sequence of the wild type prohibitin 3'UTR and the location of primers (underlined) which may be utilized for an AflIII restriction fragment length polymorphism (RFLP) assay for genotyping. The assay is run in two steps with the initial primer set P1/P2 being used for PCR amplification. The initial PCR reaction products are then run on a 2.5% agarose gel and the 852 bp band is excised and purified. The 852 bp fragment is used as the template in PCR with one of the primer sets P3/P2 or P4/P2 to produce a sub-fragment. This subfragment is purified through microspin columns (Pharmacia), and digested with AflIII. Primers P1, P3, and P4 are all sense primers. Primer P2 is an antisense primer whose sequence is 5'-GGAAGGTCTGGGTGTCATTT-3' (SEQ ID NO:19).

FIG. 3 illustrates the 5'-3' sense sequence of the prohibitin gene which begins in intron 6, contains the protein coding region of exon 7 and continues to the end of the 3'UTR. The primers P1' (SEQ ID NO:23) (forward) and P2 (SEQ ID NO:19) (reverse) are used to synthesize the PCR fragment that is used for an AflIII RFLP genotyping assay. The 1237 bp fragment (from position 93 to position 1328 in FIG. 3) that is synthesized is digested with AflIII to determine the genotype. The symbol "*" marks the beginning of the 852 bp 3'UTR coding sequence (FIG. 2), and the numbers on the right of the sequence give the base number for the 852 bp 3'UTR coding sequence. The symbol "++++++" shows the location of the constitutive AflIII site while the symbol "******" shows the location of the polymorphic site. Cleavage by AflIII is lost when the site is ATGTGT. The C to T polymorphism occurs at position 729 in the 852 bp UTR (FIG. 2) and position 1205 in this sequence (FIG. 3). Also shown on this figure are the forward P3' primer (SEQ ID NO:25) and reverse P4' primer (SEQ ID NO:26) used to synthesize the 442 bp probe used in Southern blotting experiments as described in Example 1.

DETAILED DESCRIPTION OF THE INVENTION

Figure 4:
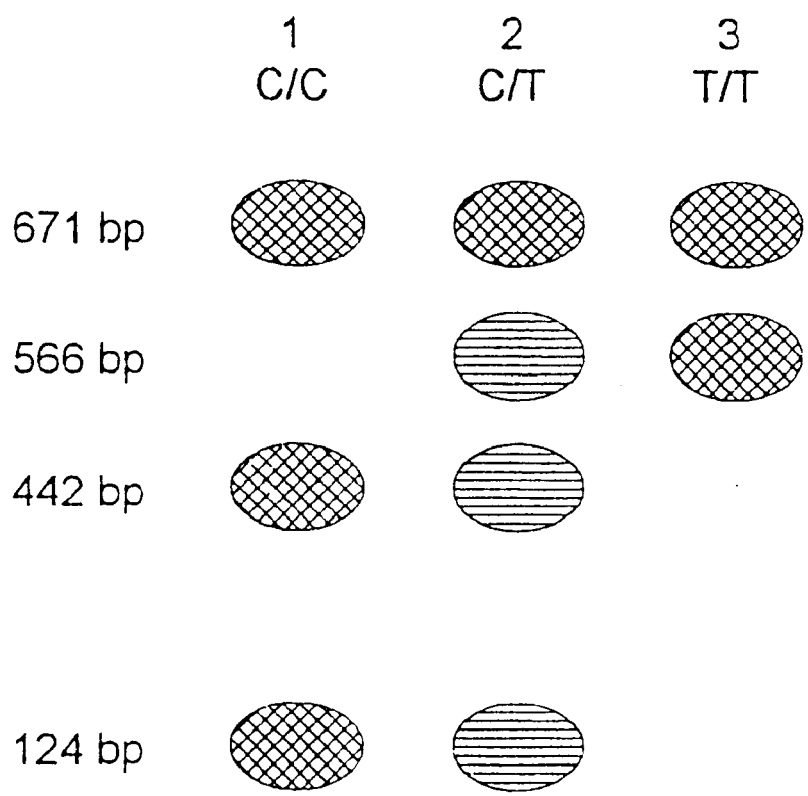
FIG. 4 illustrates the diagnostic restriction fragment length polymorphism analysis (RFLP) patterns obtained with the PCR assay as described in FIG. 3. The genotypes illustrated are as follows: 1-C/C; 2-C/T; 3-T/T. The sizes of the fragments observed are shown to the left of the figure. The 671 bp fragment is common to all genotypes. The pattern shown for the 566 bp and 442 bp fragments is also observed with genomic Southern blots using the 442 bp probe.

Based on the frequencies of the C/C, C/T, and T/T germline genotypes at position 729 (as defined in FIG. 2 of the application) in the prohibitin 3'UTR among controls and breast cancer cases, a simple test has been developed to determine the susceptibility of lifetime probability of an individual developing breast cancer. Given that the overall probability of a woman developing breast cancer in the U.S. is 12.5%, Bayes Theorem was applied to the genotypic frequencies determined on 72 breast cancer patients and 92 unaffected females (Table 1), and the resulting probability that a woman with a particular genotype will develop breast cancer over the course of her lifetime {probability= [(frequency of breast cancer patient having given genotype)×(overall probability of a woman developing breast cancer, i.e., 0.125)]÷[frequency of unaffected woman having given genotype]×100} is as follows: C/C, 10%; C/T, 17%; and T/T, approximately 50%. While the calculated percentages may vary depending on the size of the sampled population, it is expected that the disclosed percentages will provide a useful guide as to risk.

To determine a woman's probability of developing breast cancer requires only a determination of the woman's germline prohibitin genotype with regard to position 729 of the 3'UTR; that is, whether the woman is homozygous thymine (T/T) or homozygous cytosine (C/C) or heterozygous (C/T) at position 729. To determine an individual's genotype at position 729, genomic DNA can be isolated from a wide variety of patient samples using standard techniques. Preferably, the genomic DNA is isolated from either blood or buccal cell smears as described in Example 1. Following preparation of genomic DNA, the region containing base 729 of the prohibitin 3'UTR may be amplified, or the genomic DNA may be directly digested (Example 1). Like the preparation of genomic DNA, this too can be done by a wide variety of standard techniques. Preferably, this region is amplified by polymerase chain reaction ("PCR") techniques, as described in Example 1.

Preferably, following PCR amplification, a restriction fragment length polymorphism ("RFLP") analysis is conducted as described in Example 1. This analysis is based on the fact that the substitution of a T for C at position 729 in the 3'UTR results in the loss of cleavability by the restriction endonuclease AflIII at its six base recognition site which spans position 729.

Alternatively, the PCR amplified sequence at position 729 could be determined by any other means for distinguishing sequence variants such as by direct sequencing using Ampli-Cycle™ PCR kit(Perkin Elmer) or Southern blotting.

The probability that a particular genotype will result in breast cancer is as previously stated. For those who are homozygous for the C-allele (C/C) at position 729, the probability of developing breast cancer is 10%, for those who are heterozygous (C/T) the probability is 17%, and for those who are homozygous for the T-allele (T/T) the probability of a woman developing breast cancer during her lifetime is approximately 50%. These probabilities are based on the germline prohibitin genotypes of 92 control females and 72 breast cancer cases as shown in Table 1.

Being able to accurately determine a woman's genotype with respect to position 729 serves a variety of useful purposes. First and foremost, as already described above, it provides a means by which a woman's lifetime probability of developing breast cancer can be determined. For those who are diagnosed as having an increased risk, an enhanced awareness of the increased risk in conjunction with more frequent examinations may lead to an earlier detection of the cancer and an increased chance of survival. This would be particularly useful for the newborn to those up to the age of 40 who are generally not yet screened for the development of breast cancer.

The assay could also be used in genetic counseling. Where the parents are both homozygous for the T-allele, the probability of having a child with the T/T genotype is 100%.

Conversely, where the parents are both homozygous for the C-allele, the probability of having a child with the T/T genotype is 0%. Where only one parent is homozygous for the T allele, or where one or both parents are heterozygous (C/T) at position 729, the probability of having a child with the T/T genotype is somewhere between these two extremes and can be determined according to classic Mendelian genetics. Depending on their genotypes, the parents of a child could then determine the child's genotype as a newborn or even prenatally. This information could then be used as described above to determine an optimum schedule of examinations to ensure early detection and treatment.

This assay could also be used for breast cancer prognosis, the prediction of disease-free interval, long-term survivorship, and determination of therapy for both women and men.

Determining the Prohibitin Polymorphism at UTR-729

A thorough mutation analysis was first conducted on seven individual patients in which all of the tumors analyzed were diagnosed by histopathology as invasive ductal carcinomas. In order to avoid cross contamination, these analyses were done on tumor tissue and normal adjacent tissue isolated separately by microdissection from hematoxylin and eosin (H&E) stained sections. Our unpublished studies of the prohibitin 3'UTR in breast cancer cell lines and other cancer cell lines showed that the final 200 bases contained prohibitin's antiproliferative activity and was also the most heavily mutated. Thus, only the final 140 bp of the 3'UTR was examined. PCR amplication products were cloned into the TA cloning vector, and at least two clones from the tumor and two clones from normal adjacent tissue were sequenced from each patient. FIGS. 1A and 1B show an alignment of these seven tumor sequences [TN-56(T), SEQ ID NO:2; TN-78(T), SEQ ID NO:4; TN-50(T), SEQ ID NO:6; TN-1 (T), SEQ ID NO:9; TN-3(T), SEQ ID NO:11; TN-31(T), SEQ ID NO:13; and TN-94(T), SEQ ID NO:15] and adjacent normal tissue [TN-56(N), SEQ ID NO:3; TN-78(N), SEQ ID NO:5; TN-50(N), SEQ ID NO:7; TN-1(N), SEQ ID NO:10; TN-3(N), SEQ ID NO:12; TN-31(N), SEQ ID NO:14; and TN-94(N), SEQ ID NO:16]] compared to the wild-type prohibitin 3'UTR (WT) (SEQ ID NO:1) and the heavily mutated breast cancer cell line SK-BR-3 (SEQ ID NO:8) sequences in a 140 b.p. region near the 3' end of the wild-type prohibitin 3'UTR (SEQ ID NO:17).

The most frequently and only consistently altered site was the cytosine (C) at position 729 which was changed to a thymine (T) in all of the tumors. The 3'UTR sequences from the adjacent normal tissue from each of the patients is also shown directly beneath the tumor sequences in FIGS. 1A and 1B. This analysis showed that all of the normal tissue was wild-type except for demonstrating heterozygosity at position 729 of the 3'UTR.

The finding that seven out of seven normal tissue specimens adjacent to breast tumors showed heterozygosity (C/T) at position 729 in the prohibitin 3'UTR was unexpected, as prior to this time, only "C" had been found at this position in normal tissue or cell lines derived from normal tissue. Further studies were then performed to determine if the T was an "initiator" mutation responsible, at least in part, for the development of the tumor, but also found in histologically normal adjacent tissue indicating a clonal or field effect, or if the T represented a germline allelic variant (polymorphism) present in the normal population. To distinguish between the two possibilities, tests were done to determine if there were thymines at position 729 in germline tissue far removed from the tumor in breast cancer patients and in control individuals. That is, the frequency of T vs C at position 729 of the 3'UTR (UTR-729) was determined in tissue representing the germline genotype (blood sample and/or buccal cell scrapes) from these two groups.

The region containing UTR-729 is cleaved by the restriction enzyme AflIII when cytosine (C) is present in the wild type sequence. This cleavage site is lost when a thymine (T) is present. Sequencing from patient samples identified only this single change within the AflIII recognition site (FIGS. 1A and 1B). In an AflIII RFLP analysis, 70% of 92 healthy female volunteers were

TABLE 1

Genotype and allele frequencies of 3'UTR variants among controls and breast cancer cases

| | Number Frequency | | | |
|---|---|---|---|---|
| | Control Females | | Breast Cancer Patients | |
| Genotypes | | | | |
| C/C | 64 | 0.696 | 41 | 0.569 |
| C/T | 27 | 0.293 | 28 | 0.389 |
| T/T | 1 | 0.011 | 3 | 0.042 |
| Total Alleles | 92 | 1.000 | 72 | 1.000 |
| C | 155 | 0.842 | 110 | 0.764 |
| T | 29 | 0.158 | 34 | 0.236 |
| Total | 184 | 1.000 | 144 | 1.000 | homozygous C/C, 29% were heterozygous C/T, and 1.1% were homozygous T/T (Table 1). This is in contrast to 72 breast cancer patients where 4% were T/T, 39% were C/T and 57% were C/C ($\chi^2$=3.672 and p<0.159). Assuming that the data in Table 1 accurately reflect the genotypic frequencies of cases and controls in the general population and that the lifetime risk of breast cancer is 12.5%, Bayes' Theorem (Fleiss, J., *Statistical Methods for Rates and Proportions*, 2nd ed., John Wiley & Sons, New York, 1981, pp. 1–17) can be used to calculate the probability that a woman with a particular genotype will develop breast cancer over the course of her lifetime. These probabilities are: 10% for C/C, 17% for C/T, and approximately 50% for T/T. Furthermore, if 4% of all breast cancer cases are T/T, then 4% of women who will eventually get breast cancer can be identified by this simple test.

The mean age ± standard deviation for the control and cases were 40±12.9 and 55±11.5 years, respectively. The majority of the cases and controls (95%) are Caucasian females residing in Oklahoma. Potential relative risk of breast cancer was also examined in terms of the odds ratio (OR). The odds ratio for subjects having C/T and subjects having T/T combined, i.e., T carrier, was calculated as $OR_T$=[(number of breast cancer patients having C/T+ number of breast cancer patients having T/T)±(number of breast cancer patients having C/C)]±[(number of unaffected subjects having C/T+number of unaffected subjects having T/T)±(number of unaffected subjects having C/C)]. The odds ratio for subjects having T/T, i.e., homozygous T, was calculated as $OR_{T/T}$=[(number of breast cancer patients having T/T)±(number of breast cancer patients having C/C+ the number of breast cancer patients having C/T)]±[(number of unaffected subjects having T/T)±(number of unaffected subjects having C/C+the number of unaffected subjects having C/T)]. The odds ratio calculated after combining subjects carrying either C/T or T/T is about 1.7. When T/T is considered separately with C/T and C/C combined, the odds ratio is about 4.0. Again, while the calculated odds ratios may vary depending on the size of the sampled population, it is expected that the disclosed ratios will provide a useful guide as to risk.

Relevance of Polymorphism at UTR-729 to Cancer

In the U.S., a woman has a 1 in 8 (12.5%) risk of developing breast cancer during her lifetime and a 1 in 28 (3.6%) risk of dying from the disease (Boring, et al., "Cancer statistics," *CA Cancer J Clin* 44:7–26 (1994)). Approximately 10% of all breast cancers are currently classified as familial and many of these appear to be caused by germline mutations in the BRCA1 gene on chromosome 17q21 (Hall, et al., "Linkage of early onset familial breast cancer to chromosome 17q21," *Science* 250:1684–1689 (1990)) or the BRCA2 gene on chromosome 13q12–13 (Wooster, et al., "Localization of a breast cancer susceptibility gene, BRCA2, to chromosome 13q12–13," *Science* 265:2088–2090 (1994)). However, the vast majority of breast cancers are considered to be sporadic. It was originally thought that many of these sporadic cancers would also be caused by somatic mutations in familial breast cancer genes. This has not proven to be the case. Few, if any, somatic mutations of BRCA1 have been found in sporadic breast tumors (Merajver, et al, "Somatic mutations in the BRCA1 gene in sporadic ovarian tumours," *Nat Genet* 9:439–443 (1995); Hosking, et al., "A somatic BRCA1 mutation in an ovarian tumour," *Nat Genet* 9:343–344 (1995); and Futreal, et al., "BRCA1 mutations in primary breast and ovarian carcinomas," *Science* 266:120–122 (1994)). In other studies, only one out of 70 (Lancaster, et al., "BRCA2 mutations in primary breast and ovarian cancers," *Nat Genet* 13:238–240 (1996)), and one out of 100 breast cancer patients had somatic mutations in BRCA2 (Miki, et al., "Mutation analysis in the BRCA2 gene in primary breast cancers," *Nat Genet* 13:245–247 (1996); Teng, et al., "Low incidence of BRCA2 mutations in breast carcinoma and other cancers," *Nat Genet* 13:241–244 (1996)). Thus, mutations at these loci do not appear to be important in the majority of sporadic breast cancers.

Table 1 suggests that women who carry even a single germline prohibitin allele with the 729-T polymorphism are at approximately 2.0-fold increased risk for breast cancer compared to those who are homozygous for 729-C (17% vs. 10%). Furthermore, Bayes' Theorem predicts that women who are homozygous at 729-T have a 50% risk of developing breast cancer over the course of a lifetime. If the data in Table 1 are representative of all breast cancers, then approximately 4% of breast cancer cases will develop in T/T women even though they represent less than 1% of the total population. Therefore, screening women in the general population for this polymorphism will allow the identification of up to 1% of all women with a significantly higher than average risk of eventually getting breast cancer. Likewise, women who are homozygous C/C (70% of the total population) can be counseled that their probability of developing breast cancer over their lifetime is approximately 10%, or only slightly below the average risk. Furthermore, the 729-T polymorphism is inherited, which suggests that a substantial subset of breast cancers previously considered to be sporadic (i.e., those developing in C/T and T/T women or 43% overall), have a hereditary component. From the relative proportions of C/C, C/T, and T/T individuals in the general population (Table 1), it can be assumed that most homozygous T/T women have heterozygous C/T parents. In this case, the probability of a T/T woman with breast cancer having a sibling who is also T/T is 1 in 4. This is precisely the risk of developing breast cancer for women who have first degree relatives with the disease (Boring, et al., *CA Cancer J Clin* 44:7–26 (1994)).

Example 1

Diagnostic Assay Methodology

The diagnostic assay for determining susceptibility of breast cancer based on the sequence of the 3'UTR of the prohibitin gene is described below.

Sample Collection

Blood samples (approx. 10 ml) were collected by routine venipuncture into tubes containing anticoagulant.

Buccal cell smears were collected using sterile cytology brushes (type H—Histobrush, 174–600; Spectrum Laboratories, Dallas, Tex.). The study participant was instructed to twirl the brush on the inner cheek for 30 seconds on each side. The brush was then inserted into a sterile collection tube, tightly capped, and stored at 4° C. prior to DNA template preparation.

DNA Preparation

The DNA from blood samples was prepared using the PureGene Kit (Gentra, Minneapolis, Minn.).

The DNA from buccal cell smears was isolated using a method described by Horrigan, et al., "Polymerase chain reaction-based diagnosis of Del(5q) in acute myeloid leukemia and myelodysplastic syndrome identifies a minimal deletion interval," *Blood* 88:2665–2670 (1996), which is a modification of a method originally published by Richards, et al., "Multiplex PCR amplification from the CFTR gene using DNA prepared from buccal brushes/swabs," *Hum Mol Genet* 2:159–160 (1993). The cytology brush was transferred to a 1.5 ml tube containing 0.6 ml of 50 mM sterile NaOH. The handle of the brush was clipped, and the lid was closed. After vortexing for 30 seconds, the sample was heated to 95° C. for 5 minutes. The tube was vortexed again, and the brush was drained to recover residual liquid prior to removal from the tube. The solution was neutralized by adding 0.06 ml of 1 mM Tris, pH=8.0. After thorough mixing, the sample was stored at −20° C. The assay can also be performed on high molecular weight DNA purified from skin, hair follicles, and virtually any other tissue source as well as from fibroblast or lymphoblast cell lines. In this case, the DNA can be prepared using the PureGene kit (Gentra, Minneapolis, Minn.), or any similar method, in accordance with the manufacturer's instructions.

Polymerase Chain Reaction

PCR reactions were run on 0.1 $\mu$g of genomic DNA purified from blood or 0.010 ml of buccal smear extract using Taq Gold polymerase (Perkin Elmer, Foster City, Calif.). The reaction conditions used were as follows: 10 mM Tris-HCl, pH=8.0, 50 mM KCl, 1.5 mM MgCl, 100–200 $\mu$M each of DATP, dGTP, dTTP, and dCTP, 0.1% Triton X-100, 0.5–1.0 units Taq Gold polymerase, and 100 ng of each primer in a 50-$\mu$l reaction mix.

In one form of the assay, as illustrated in FIG. 2 and SEQ ID NO:17, an 852 bp 3'UTR synthesized with primers 5'-CCCAGAAATCACTGTG-3' (primer P1, sense) (SEQ ID NO:20) and primer P2 (SEQ ID NO:19) is gel purified and a secondary PCR product is synthesized using the primers 5'-TGAGTCCTGTTGAAGACTTCC-3' (primer P3, sense) (SEQ ID NO:18) and 5'-GGAAGGTCTGGGTGTCATTT-3' (primer P2, antisense)(SEQ ID NO:19).

Restriction Fragment Length Polymorphism Analyses

The PCR products were digested with the restriction enzyme AflIII using the buffer and conditions recommended by the manufacturer (New England Biolabs, Cambridge, Mass.). All digestions for a group of individual samples were performed using a diluted master mix. Controls with confirmed sequence were included with each series of digests. The digestion products were separated by electrophoresis on 20% acrylamide gels, stained with ethidium bromide and visualized by ultraviolet light.

Alternatively, high molecular weight DNAs purified by using the PureGene kit were analyzed for restriction fragment length polymorphisms by Southern blotting. Generally, 10–15 μg of DNA was digested with the restriction enzyme AflIII (New England Biolabs) at 37° C. for 16 hours using the manufacturer supplied buffer. The digests were terminated by precipitating the DNA by adding 1/10 volume 3M sodium acetate and 2 volumes of absolute ethanol. Following resuspension in water and addition of loading dye (Promega 6X), the samples were loaded into a 1% agarose gel, and electrophoresis was performed until the bromophenol blue loading dye reached the bottom of the gel. Gels were then denatured in 0.5 M NaOH/1.5M NaCl for 30 minutes followed by neutralization in 0.5M Tris/1.5 M NaCl (pH=7.0). A Southern blot was then carried out by capillary transfer to Hybond membrane (Amersham, Arlington Heights, Ill.). The DNA was fixed to the membrane either by baking at 80° C. or crosslinking with ultraviolet light.

The RFLP was detected by probing with a nucleic acid fragment containing the prohibitin 3'UTR. The routinely used probe was a 442 bp nucleic acid fragment that lies immediately 5' to the polymorphic AflIII cut site. It was synthesized by PCR using a full length 3'UTR clone for template and primers P3' and P4' (FIG. 3). The probe was labeled using a random primer labeling kit (Pharmacia, Piscataway, N.J.). The membranes were hybridized at least 12 hours at 65° C. and washed at the same temperature under high stringency. The filter was then exposed to x-ray film or a phosphoimager screen to display the RFLP for interpretation. Alternatively, a 124 bp fragment 3' to the polymorphic AflIII site, as well as the 566 bp fragment synthesized with P3' and P2 primers (FIG. 3) may be used as a probe. Any of these probes will display an RFLP that distinguishes the different genotypes. Southern blots probed with the 442 bp probe displayed the 566 bp and 442 bp banding pattern shown in FIG. 4.

The substitution of a T for C at position 729 (FIG. 2) in the 3'UTR results in the loss of cleavability by AflIII at its six base recognition sequence. Our analyses of mutated breast tumors (7), breast cancer cell lines (3), and buccal cell scrapes from homozygous T breast cancer patients (7) show that the C to T at 729 is the only change in the recognition site thus far detected that is responsible for loss of AflIII cutting. Homozygous C individuals have both alleles cut at the polymorphic site, while alleles of homozygous T individuals do not cut. Heterozygous individuals have one allele of each, C and T.

Example 2

Alternative Diagnostic Assay Method

An alternative assay was performed as given in Example 1, with the exception that the secondary PCR product was synthesized using the sense primer P4, 5'-GGATGGACTTGTATAG-3' (SEQ ID NO:21) and the antisense primer 5'-GGAAGGTCTGGGTGTCATTT-3' (primer P2, antisense)(SEQ ID NO:19).

Example 3

Alternative Diagnostic Assay Method

An alternative assay was performed as given in Example 1, with the exception that, as illustrated in the 1237 bp genomic sequence given in FIG. 3 and SEQ ID NO:22, the primers utilized were 5'-AAGGTGGCTTTCTGGTGAAG-3' (primer P1', sense)(SEQ ID NO:23) and 5'-GGAAGGTCTGGGTGTCATTT-3' (primer P2, antisense)(SEQ ID NO:19). In this assay using SEQ ID NO:22, the base at position 1205 corresponds to the position 729 in SEQ ID NO:17.

FIG. 4 illustrates the pattern of bands produced in this assay for each genotype. Utilizing the sense primer SEQ ID NO:23 and antisense primer SEQ ID NO:19, the RFLP pattern for a homozygous C individual (C/C) shows that for both DNA strands, the 566 bp measured from the constitutive AflIII site to the end of the 3'UTR was cut at position 729/1205 into two distinct bands of 442 bp and 124 bp. A homozygous T individual (T/T) produced one band of 566 bp measured from the constitutive AflIII site to the end of the 3'UTR which was uncut at position 729/1205 on both DNA strands. The heterozygous individual (C/T) gave three distinct bands, showing that for one DNA strand, the 566 bp measured from the constitutive AflIII site to the end of the 3'UTR was cut at position 729/1205 into two distinct bands of 442 bp and 124 bp, and for the other DNA strand, one band of 566 bp measured from the constitutive AflIII site to the end of the 3'UTR was uncut at position 729/1205. In this assay, a band common to all genotypes is the 671 bp fragment measured from the 5' end of the PCR product to the constitutive cut site.

This method is a single step process that shows 100% correlation with Southern blot results.

Example 4

Alternative Approaches

The predictive value of this assay involves determining the germline genotype of an individual at position 729 in the prohibitin 3'UTR. There are many potential specific methods that can be used to accomplish this task. We have primarily used the RFLP described in Example 1 and DNA sequencing to collect our data. However, any other methods based on single base oligonucleotide mismatch screening (Jupe, E. R. and Zimmer, E. A., "Assaying differential ribosomal RNA gene expression with allele-specific oligonucleotide probes," In *Methods in Enzymology-Molecular Evolution: Producing the Biochemical Data*, Academic Press, pp. 541–552, 1993), allele specific PCR amplification (Allen, et al., *BioTechniques* 19:454 (1995); Ault, G., *J Virological Methods* 46:145–156 (1994); Tada, M., *Cancer Research* 53:2472–2474 (1993); Huang, *Nucleic Acids Research* 20:4567–4573 (1992); Sommer, *BioTechniques* 12:82–87 (1992); and Kwok, *Nucleic Acids Research* 18:999–1005 (1990)), or a method employing a high specificity thermostable ligase (Ampligase, Epicenter Technologies) could be applied for detection of the polymorphism. In addition, any method currently in use such as single strand conformation polymorphisms or denaturing gradient gel electrophoresis, or any method developed in the future for detecting single base changes, could also be applied to the detection of these genotypes. This test could also be performed starting with RNA. In this case, the RNA would be analyzed directly by sequencing or converted to cDNA using reverse transcriptase (Castles, et al., *BioTechniques* 21:425–428 (1996), followed by PCR and any method capable of detecting single base changes.

Example 5

Diagnostic Assay for Hereditary Breast Cancer in Men

The C/T polymorphism at position 729 in the prohibitin 3'UTR is also useful for the diagnosis of susceptibility to breast cancer in men.

A portion of genomic DNA isolated from a male patient diagnosed with breast cancer was examined according to the assay given in Example 3. The patient's genotype was identified as T/T, which corresponds to an increased risk for breast cancer.

We claim:

1. A method for determining risk of a hereditary breast cancer, comprising the steps of:
   a. determining the base identity of a portion of genomic DNA from a patient cell sample, said genomic DNA comprising a prohibitin gene comprising a 3' untranslated region, said portion corresponding to position 729 as defined in SEQ ID NO:17 of said prohibitin gene in said 3' untranslated region; and
   b. correlating said base identity with a risk for hereditary breast cancer.

2. The method of claim 1, wherein the base identity of position 729 is determined by sequencing a portion of said portion of 3' untranslated region of said prohibitin gene containing said position 729.

3. The method of claim 1, wherein base identity of said position 729 is determined by detection of single base matches or mismatches between said portion of 3' untranslated region and C-allele prohibitin.

4. The method of claim 1, wherein the base identity of position 729 is determined by digesting said portion of 3' untranslated region of said prohibitin gene with a restriction endonuclease appropriate to determine the base identity of said position 729.

5. The method of claim 4, wherein said restriction endonuclease is AflIII, and whereby it is determined that a cleavage site affected by AflIII is present when position 729 is cytosine.

6. The method of claim 5, further comprising the steps of:
   a. separating said digested portion of 3' untranslated region DNA strands;
   b. fixing said separated digested 3' untranslated region DNA strands onto a membrane;
   c. hybridizing said separated digested 3' untranslated region DNA strands with at least one labeled nucleic acid probe, wherein said labeled nucleic acid probe can complementarily bind to said fixed separated digested 3' untranslated region DNA strands and can identify whether cleavage at said position 729 occurred; and
   d. detecting if said labeled nucleic acid probe has bound to said fixed separated digested 3' untranslated region DNA strands, wherein said patient is at risk for hereditary breast cancer if said labeled nucleic acid probe bound to said fixed separated digested 3' untranslated region DNA strands indicates cleavage at said position 729 did not occur.

7. The method of claim 1, wherein said base identity is determined by examining an RNA fraction from said patient cell sample, whereby the identity of said genomic DNA at said position 729 can be determined.

8. The method of claim 1, wherein a lifetime risk for developing breast cancer is assessed to be greater than that of the unaffected relevant population when the base identity at said position 729 is homozygous for thymine.

9. The method of claim 1, wherein a lifetime risk for developing breast cancer is assessed to be greater than that of the unaffected relevant population but less than that of an individual who is homozygous for thymine when the base identity at said position 729 is heterozygous cytosine/thymine.

10. The method of claim 1, wherein a lifetime risk for developing breast cancer is assessed to be less than or equal to the unaffected relevant population when the base identity at said position 729 is homozygous cytosine.

11. A method for determining the risk for hereditary breast cancer in a human patient, comprising the steps of:
  a. isolating a portion of double-stranded genomic DNA from a patient cell sample, said genomic DNA comprising a prohibitin gene comprising a 3' untranslated region;
  b. separating said double-stranded genomic DNA into a first single-stranded genomic DNA and a second single-stranded genomic DNA in a first reaction zone;
  c. providing a sense primer to said reaction zone, said reaction zone having conditions favorable for hybridization between said first single-stranded genomic DNA and said sense primer;
  d. simultaneously providing an antisense primer to said reaction zone, said reaction zone having conditions favorable for hybridization between said second single-stranded genomic DNA and said antisense primer;
  e. making multiple copies of said portion of double-stranded genomic DNA by polymerase chain reaction methodology to form synthesized double-stranded DNA;
  f. determining the base identity of position 729 as defined by SEQ ID NO:17 for said 3' untranslated region DNA strands; and
  g. correlating said base identity with a risk for hereditary breast cancer, wherein said patient is at lowest risk with homozygous C/C, intermediate risk with heterozygous C/T, and greatest risk with homozygous T/T at said position 729.

12. The method of claim 11, wherein said sense primer comprises SEQ ID NO:18.

13. The method of claim 11, wherein said sense primer comprises SEQ ID NO:20.

14. The method of claim 11, wherein said sense primer comprises SEQ ID NO:21.

15. The method of claim 11, wherein said sense primer comprises SEQ ID NO:23.

16. The method of claim 11, wherein said antisense primer comprises SEQ ID NO:19.

17. The method of claim 12, wherein said antisense primer comprises SEQ ID NO:19.

18. The method of claim 13, wherein said antisense primer comprises SEQ ID NO:19.

19. The method of claim 14, wherein said antisense primer comprises SEQ ID NO:19.

20. The method of claim 15, wherein said antisense primer comprises SEQ ID NO:19.

21. The method of claim 18, further comprising, prior to step f, purifying to form an 852 bp fragment and performing secondary polymerase chain reaction using sense primer comprising SEQ ID NO:18 and antisense primer comprising SEQ ID NO:19 to form synthesized double-stranded DNA.

22. The method of claim 11, wherein base identity of said position 729 is determined by sequencing.

23. The method of claim 11, wherein base identity of said position 729 is determined by detection of single base matches or mismatches between said synthesized double-strand DNA and C-allele prohibitin.

24. The method of claim 11, wherein base identity of said position 729 is determined by restriction fragment length polymorphism.

25. The method of claim 11 further comprising digesting said synthesized double-stranded DNA with restriction endonuclease AflIII which cleaves said untranslated region at said base 729 when said base is cytosine.

26. The method of claim 21 further comprising digesting said synthesized double-stranded DNA with restriction endonuclease AflIII which cleaves said untranslated region at said base 729 when said base is cytosine.

27. The method of claim 25, further comprising the steps of:
  h. separating said digested synthesized double-stranded DNA strands;
  i. fixing said separated digested synthesized double-stranded DNA strands onto a membrane;
  j. hybridizing said separated digested synthesized double-stranded DNA strands with at least one labeled nucleic acid probe, wherein said labeled nucleic acid probe can complementarily bind to said fixed separated digested synthesized double-stranded DNA strands and can identify whether cleavage at said position 729 occurred; and
  k. detecting if said labeled nucleic acid probe has bound to said fixed separated digested synthesized double-stranded DNA strands, wherein said patient is at risk for hereditary breast cancer if said labeled nucleic acid probe bound to said fixed separated digested synthesized double-stranded DNA strands indicates cleavage at said position 729 did not occur.

28. The method of claim 25, further comprising the steps of:
  h. separating said digested synthesized double-stranded DNA strands; and
  i. visualizing said digested synthesized double-stranded DNA fragment pattern by ethidium bromide staining and ultraviolet photography.

29. The method of claim 26, further comprising the steps of:
  h. separating said digested synthesized double-stranded DNA strands;
  i. fixing said separated digested synthesized double-stranded DNA strands onto a membrane;
  j. hybridizing said separated digested synthesized double-stranded DNA strands with at least one labeled nucleic acid probe, wherein said labeled nucleic acid probe can complementarily bind to said fixed separated digested synthesized double-stranded DNA strands and can identify whether cleavage at said position 729 occurred; and
  k. detecting if said labeled nucleic acid probe has bound to said fixed separated digested synthesized double-stranded DNA strands, wherein said patient is at risk for hereditary breast cancer if said labeled nucleic acid probe bound to said fixed separated digested synthesized double-stranded DNA strands indicates cleavage at said position 729 did not occur.

30. The method of claim 26, further comprising the steps of:
  h. separating said digested synthesized double-stranded DNA strands; and
  i. visualizing said digested synthesized double-stranded DNA fragment pattern by ethidium bromide staining and ultraviolet photography.

31. The method of claim 11, wherein said portion of genomic DNA is SEQ ID NO:22.

32. The method of claim 31, wherein said sense primer SEQ ID NO:23 is used to amplify SEQ ID NO:22.

33. The method of claim 31, wherein said antisense primer SEQ ID NO:19 is used to amplify SEQ ID NO:22.

34. The method of claim 32, wherein said antisense primer SEQ ID NO:19 is used to amplify SEQ ID NO:22.

35. The method of claim 34, wherein base identity of said position 729 is determined by sequencing.

36. The method of claim 34, wherein base identity of said position 729 is determined by detection of single base mismatches between said synthesized double-strand DNA and C-allele prohibitin.

37. The method of claim 34, wherein base identity of said position 729 is determined by restriction fragment length polymorphism.

38. The method of claim 34 further comprising digesting said synthesized double-stranded DNA with restriction endonuclease AflIII which cleaves said untranslated region at said base 729 when said base is cytosine.

39. The method of claim 38, further comprising the steps of:
   h. separating said digested synthesized double-stranded DNA strands;
   i. fixing said separated digested synthesized double-stranded DNA strands onto a membrane;
   j. hybridizing said separated digested synthesized double-stranded DNA strands with at least one labeled nucleic acid probe, wherein said labeled nucleic acid probe can complementarily bind to said fixed separated digested synthesized double-stranded DNA strands and can identify whether cleavage at said position 729 occurred; and
   k. detecting if said labeled nucleic acid probe has bound to said fixed separated digested synthesized double-stranded DNA strands, wherein said patient is at risk for hereditary breast cancer if said labeled nucleic acid probe bound to said fixed separated digested synthesized double-stranded DNA strands indicates cleavage at said position 729 did not occur.

40. The method of claim 38, further comprising the steps of:
   h. separating said digested synthesized double-stranded DNA strands; and
   i. visualizing said digested synthesized double-stranded DNA fragment pattern by ethidium bromide staining and ultraviolet photography.

41. A method for determining the risk for hereditary breast cancer in a human patient comprising the steps of:
   a. determining the sequence of RNA isolated from said patient in a region which is a transcription of a portion of genomic DNA, said genomic DNA comprising a prohibitin gene comprising an untranslated region, said portion corresponding to position 729 as defined in SEQ ID NO:17 of said prohibitin gene in said untranslated region; and
   b. correlating said base identity with a risk for hereditary breast cancer.

* * * * *

SEQUENCE LISTING (1) GENERAL INFORMATION:

(iii) NUMBER OF SEQUENCES: 25

(2) INFORMATION FOR SEQ ID NO:1:

(i) SEQUENCE CHARACTERISTICS:
      (A) LENGTH: 140 base pairs
      (B) TYPE: nucleic acid
      (C) STRANDEDNESS: double
      (D) TOPOLOGY: linear (ii) MOLECULE TYPE: DNA (genomic)

(vi) ORIGINAL SOURCE:
      (A) ORGANISM: Homo sapiens (ix) FEATURE:
      (A) NAME/KEY: misc_feature
      (B) LOCATION: 1..140
      (D) OTHER INFORMATION: /note= "wild type (WT)"

(xi) SEQUENCE DESCRIPTION: SEQ ID NO:1:

```
AGTGGAATTC CAACTTGAAG GATTGCATCC TGCTGGGGCT GAACATGCCT GCCAAAGAYG     60

TGTCCGACCT ACGTTCCTGG CCCCCTCGTT CAGAGACTGC CCTTCTCACG GGCTCTATGC    120

CTGCACTGGG AAGGAAACAA                                                140
```

(2) INFORMATION FOR SEQ ID NO:2:

(i) SEQUENCE CHARACTERISTICS:
      (A) LENGTH: 140 base pairs
      (B) TYPE: nucleic acid
      (C) STRANDEDNESS: double
      (D) TOPOLOGY: linear (ii) MOLECULE TYPE: DNA (genomic)

(vi) ORIGINAL SOURCE:
      (A) ORGANISM: Homo sapiens (ix) FEATURE:
      (A) NAME/KEY: misc_feature
      (B) LOCATION: 1..140
      (D) OTHER INFORMATION: /note= "TN-56 (tumor)"

(xi) SEQUENCE DESCRIPTION: SEQ ID NO:2:

```
AGTGGAATTC CAACTTGAAG GATTGCATCC TGCAGGGGCT GAACATGCCT GCCAAAGATG     60

TGTCCGACCT ACGTTCCTGG CCCCCTCGTT CAGAGACTGC CCTTCTCACG GGCTCTATGC    120
```

CTGCACTGGG AAGGAAACAA                                                    140

(2) INFORMATION FOR SEQ ID NO:3:

(i) SEQUENCE CHARACTERISTICS:
        (A) LENGTH: 140 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Homo sapiens (ix) FEATURE:
        (A) NAME/KEY: misc_feature
        (B) LOCATION: 1..140
        (D) OTHER INFORMATION: /note= "TN-56 (normal)"

(xi) SEQUENCE DESCRIPTION: SEQ ID NO:3:

AGTGGAATTC CAACTTGAAG GATTGCATCC TGCTGGGGCT GAACATGCCT GCCAAAGAYG    60

TGTCCGACCT ACGTTCCTGG CCCCCTCGTT CAGAGACTGC CCTTCTCACG GGCTCTATGC   120

CTGCACTGGG AAGGAAACAA                                                140

(2) INFORMATION FOR SEQ ID NO:4:

(i) SEQUENCE CHARACTERISTICS:
        (A) LENGTH: 140 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Homo sapiens (ix) FEATURE:
        (A) NAME/KEY: misc_feature
        (B) LOCATION: 1..140
        (D) OTHER INFORMATION: /note= "TN-78 (tumor)"

(xi) SEQUENCE DESCRIPTION: SEQ ID NO:4:

AGTGGAATTC CAACTTGAAG GATTGCATCC TGCAGGGGCT GAACATGCCT GCCAAAGATG    60

TGTCCGACCT ACGTTCCTGG CCCCCTCGTT CAGAGACTGC CCTTCTCACG GGCTCTATGC   120

CTGCACTGGG AAGGAAACAA                                                140

(2) INFORMATION FOR SEQ ID NO:5:

(i) SEQUENCE CHARACTERISTICS:
        (A) LENGTH: 140 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Homo sapiens (ix) FEATURE:
        (A) NAME/KEY: misc_feature
        (B) LOCATION: 1..140
        (D) OTHER INFORMATION: /note= "TN-78 (normal)"

(xi) SEQUENCE DESCRIPTION: SEQ ID NO:5:

AGTGGAATTC CAACTTGAAG GATTGCATCC TGCTGGGGCT GAACATGCCT GCCAAAGAYG    60

```
TGTCCGACCT ACGTTCCTGG CCCCCTCGTT CAGAGACTGC CCTTCTCACG GGCTCTATGC      120

CTGCACTGGG AAGGAAACAA                                                   140
```

(2) INFORMATION FOR SEQ ID NO:6:

(i) SEQUENCE CHARACTERISTICS:
        (A) LENGTH: 140 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Homo sapiens (ix) FEATURE:
        (A) NAME/KEY: misc_feature
        (B) LOCATION: 1..140
        (D) OTHER INFORMATION: /note= "TN-50 (tumor)"

(xi) SEQUENCE DESCRIPTION: SEQ ID NO:6:

```
AGTGGAATTC CAACTTGAAG GATTGCATCC TGCTGGGGCT GAACATGCCT GCCAAAGATG       60

TGTCTGACCT ACGTTCCTGG CCCCCTCGTT CAGAGACTGC CCTTCTCACG GGCTCTATGC      120

CTGCACTGGG AAGGAAACAA                                                   140
```

(2) INFORMATION FOR SEQ ID NO:7:

(i) SEQUENCE CHARACTERISTICS:
        (A) LENGTH: 140 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Homo sapiens (ix) FEATURE:
        (A) NAME/KEY: misc_feature
        (B) LOCATION: 1..140
        (D) OTHER INFORMATION: /note= "TN-50 (normal)"

(xi) SEQUENCE DESCRIPTION: SEQ ID NO:7:

```
AGTGGAATTC CAACTTGAAG GATTGCATCC TGCTGGGGCT GAACATGCCT GCCAAAGAYG       60

TGTCCGACCT ACGTTCCTGG CCCCCTCGTT CAGAGACTGC CCTTCTCACG GGCTCTATGC      120

CTGCACTGGG AAGGAAACAA                                                   140
```

(2) INFORMATION FOR SEQ ID NO:8:

(i) SEQUENCE CHARACTERISTICS:
        (A) LENGTH: 137 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Homo sapiens (xi) SEQUENCE DESCRIPTION: SEQ ID NO:8:

```
AGTGGAATTC CAACTTGAAG TATTGAATCC TTCTGGGGCT AAACATGCCT GCCAAAGATG       60

TGTACATCCT GTGTTCCTGG CTTCCTTGTT CAGAGACTGC TCTTCTCCAG GGCTCTGTGC      120

CTGTGCTTTG AAAACAG                                                     137
```

(2) INFORMATION FOR SEQ ID NO:9:

(i) SEQUENCE CHARACTERISTICS:
        (A) LENGTH: 142 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Homo sapiens (ix) FEATURE:
        (A) NAME/KEY: misc_feature
        (B) LOCATION: 1..142
        (D) OTHER INFORMATION: /note= "TN-1 (tumor)"

(xi) SEQUENCE DESCRIPTION: SEQ ID NO:9:

```
GGAATAATTC CAAGCTTGAA TGTCCAATCC TTCTGGGGTT TCTAAAGATC CTGCCAAAGA      60

TGTGTACATC CTGTGTTCCT GGCTTCCTTG TTCGAGAACG ACTCTTCTCC ACGGCTCTGT     120

GCCTGTGCTT TGAAGGAAAC AA                                             142
```

(2) INFORMATION FOR SEQ ID NO:10:

(i) SEQUENCE CHARACTERISTICS:
        (A) LENGTH: 140 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Homo sapiens (ix) FEATURE:
        (A) NAME/KEY: misc_feature
        (B) LOCATION: 1..140
        (D) OTHER INFORMATION: /note= "TN-1 (normal)"

(xi) SEQUENCE DESCRIPTION: SEQ ID NO:10:

```
AGTGGAATTC CAACTTGAAG GATTGCATCC TGCTGGGGCT GAACATGCCT GCCAAAGAYG      60

TGTCCGACCT ACGTTCCTGG CCCCCTCGTT CAGAGACTGC CCTTCTCACG GGCTCTATGC     120

CTGCACTGGG AAGGAAACAA                                                140
```

(2) INFORMATION FOR SEQ ID NO:11:

(i) SEQUENCE CHARACTERISTICS:
        (A) LENGTH: 135 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Homo sapiens (ix) FEATURE:
        (A) NAME/KEY: misc_feature
        (B) LOCATION: 1..135
        (D) OTHER INFORMATION: /note= "TN-3 (tumor)"

(xi) SEQUENCE DESCRIPTION: SEQ ID NO:11:

```
AATGGAATTC CAACTTGAAG TATTGAATCC TTCTGGCTAA ACATGCCTGC CAAAGATGTG      60

TACATCCTGT GTTCCTGGCT TCCTTGTTCA GAGACTGCTC TTCTCCAGGG CTCTGTGCCT     120
```

```
GTGCAAAGAA AATAG                                                          135

(2) INFORMATION FOR SEQ ID NO:12:

(i) SEQUENCE CHARACTERISTICS:
        (A) LENGTH: 140 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Homo sapiens (ix) FEATURE:
        (A) NAME/KEY: misc_feature
        (B) LOCATION: 1..140
        (D) OTHER INFORMATION: /note= "TN-3 (normal)"

(xi) SEQUENCE DESCRIPTION: SEQ ID NO:12:

AGTGGAATTC CAACTTGAAG GATTGCATCC TGCTGGGGCT GAACATGCCT GCCAAAGAYG    60

TGTCCGACCT ACGTTCCTGG CCCCCTCGTT CAGAGACTGC CCTTCTCACG GGCTCTATGC   120

CTGCACTGGG AAGGAAACAA                                                140

(2) INFORMATION FOR SEQ ID NO:13:

(i) SEQUENCE CHARACTERISTICS:
        (A) LENGTH: 137 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Homo sapiens (ix) FEATURE:
        (A) NAME/KEY: misc_feature
        (B) LOCATION: 1..137
        (D) OTHER INFORMATION: /note= "TN-31 (tumor)"

(xi) SEQUENCE DESCRIPTION: SEQ ID NO:13:

AATGGAATTC CAACTTGAAG TATTGAATCC TTCTGGGGCT AAACATGCCT GCCAAAGATG    60

TGTACATCCT GTGTTCCTGG CTTCCTTGTT CAGAGACTGC TCTTCTCCAG GGCTCTGTGC   120

CTGTGCTTTG AAAATAG                                                   137

(2) INFORMATION FOR SEQ ID NO:14:

(i) SEQUENCE CHARACTERISTICS:
        (A) LENGTH: 140 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Homo sapiens (ix) FEATURE:
        (A) NAME/KEY: misc_feature
        (B) LOCATION: 1..140
        (D) OTHER INFORMATION: /note= "TN-31 (normal)"

(xi) SEQUENCE DESCRIPTION: SEQ ID NO:14:

AGTGGAATTC CAACTTGAAG GATTGCATCC TGCTGGGGCT GAACATGCCT GCCAAAGAYG    60
```

TGTCCGACCT ACGTTCCTGG CCCCCTCGTT CAGAGACTGC CCTTCTCACG GGCTCTATGC    120

CTGCACTGGG AAGGAAACAA                                                140

(2) INFORMATION FOR SEQ ID NO:15:

(i) SEQUENCE CHARACTERISTICS:
        (A) LENGTH: 140 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Homo sapiens (ix) FEATURE:
        (A) NAME/KEY: misc_feature
        (B) LOCATION: 1..140
        (D) OTHER INFORMATION: /note= "TN-94 (tumor)"

(xi) SEQUENCE DESCRIPTION: SEQ ID NO:15:

AATGGAATTC CTTCTTGAAG TATTGAATCC TTCTGGGGCT AAACATGCCT GCCAAAGATG     60

TGTACATCCT GTGTTCCTGG CTTCCTTGTT CAGAGACTGC TCTTGTCCAG GGCTCTGTGC    120

CTGTGGTTTG AAGGAAACAA                                                140

(2) INFORMATION FOR SEQ ID NO:16:

(i) SEQUENCE CHARACTERISTICS:
        (A) LENGTH: 140 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Homo sapiens (ix) FEATURE:
        (A) NAME/KEY: misc_feature
        (B) LOCATION: 1..140
        (D) OTHER INFORMATION: /note= "TN-94 (normal)"

(xi) SEQUENCE DESCRIPTION: SEQ ID NO:16:

AGTGGAATTC CAACTTGAAG GATTGCATCC TGCTGGGGCT GAACATGCCT GCCAAAGAYG     60

TGTCCGACCT ACGTTCCTGG CCCCCTCGTT CAGAGACTGC CCTTCTCACG GGCTCTATGC    120

CTGCACTGGG AAGGAAACAA                                                140

(2) INFORMATION FOR SEQ ID NO:17:

(i) SEQUENCE CHARACTERISTICS:
        (A) LENGTH: 852 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Homo sapiens (xi) SEQUENCE DESCRIPTION: SEQ ID NO:17:

CCCAGAAATC ACTGTGAAAT TTCATGATTG GCTTAAAGTG AAGGAAATAA AGGTAAAATC     60

ACTTCAGATC TCTAATTAGT CTATCAAATG AAACTCTTTC ATTCTTCTCA CATCCATCTA    120

-continued

```
CTTTTTTATC CACCTCCCTA CCAAAAATTG CCAAGTGCCT ATGCAAACCA GCTTTAGGTC        180

CCAATTCGGG GCCTGCTGGA GTTCCGGCCT GGGCACCAGC ATTTGGCAGC ACGCAGGCGG        240

GGCAGTATGT GATGGACTGG GGAGCACAGG TGTCTGCCTA GATCCACGTG TGGCCTCCGT        300

CCTGTCACTG ATGGAAGGTT TGCGGATGAG GGCATGTGCG GCTGAACTGA GAAGGCAGGC        360

CTCCGTCTTC CCAGCGGTTC CTGTGCAGAT GCTGCTGAAG AGAGGTGCCG GGAGGGGCA        420

GAGAGGAAGT GGTCTGTCTG TTACCATAAG TCTGATTCTC TTTAACTGTG TGACCAGCGG        480

AAACAGGTGT GTGTGAACTG GCACAGATT GAAGAATCTG CCCCTGTTGA GGTGGGTGGG        540

CCTGACTGTT GCCCCCCAGG GTCCTAAAAC TTGGATGGAC TTGTATAGTG AGAGAGGAGG        600

CCTGGACCGA GATGTGAGTC CTGTTGAAGA CTTCCTCTCT ACCCCCCACC TTGGTCCCTC        660

TCAGATACCC AGTGGAATTC CAACTTGAAG GATTGCATCC TGCTGGGGCT GAACATGCCT        720

GCCAAAGACG TGTCCGACCT ACGTTCCTGG CCCCCTCGTT CAGAGACTGC CCTTCTCACG        780

GGCTCTATGC CTGCACTGGG AAGGAAACAA ATGTGTATAA ACTGCTGTCA ATAAATGACA        840

CCCAGACCTT CC                                                          852
```

(2) INFORMATION FOR SEQ ID NO:18:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA primer"

(xi) SEQUENCE DESCRIPTION: SEQ ID NO:18:

```
TGAGTCCTGT TGAAGACTTC C                                                  21
```

(2) INFORMATION FOR SEQ ID NO:19:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA primer"

(iv) ANTI-SENSE: YES (xi) SEQUENCE DESCRIPTION: SEQ ID NO:19:

```
GGAAGGTCTG GGTGTCATTT                                                    20
```

(2) INFORMATION FOR SEQ ID NO:20:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA primer"

(xi) SEQUENCE DESCRIPTION: SEQ ID NO:20:

```
CCCAGAAATC ACTGTG                                                        16
```

(2) INFORMATION FOR SEQ ID NO:21:

(i) SEQUENCE CHARACTERISTICS:
    (A) LENGTH: 16 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "DNA primer"

(xi) SEQUENCE DESCRIPTION: SEQ ID NO:21:

```
GGATGGACTT GTATAG                                                 16
```

(2) INFORMATION FOR SEQ ID NO:22:

(i) SEQUENCE CHARACTERISTICS:
        (A) LENGTH: 1328 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: 5'clip
        (B) LOCATION: 1..477

(xi) SEQUENCE DESCRIPTION: SEQ ID NO:22:

```
AGGACTGGTG GGCAATGTGC TCTGCTTCCC CCCGCTTCCC CCGCTAGCCA TCAGGAGGAA     60
GTAAACTCCC CGAGTTCCTT CAGGAGCCTG GGAAGGTGGC TTTCTGGTGA AGGGCCTTTG    120
GTTGTAGCCT GACATGCGGT GCCCTGAGGT TTGATCTTTG TCTCCACCTC CATTCTTTTA    180
GGCTGAGCAA CAGAAAAAGG CGGCCATCAT CTCTGCTGAG GGCGACTCCA AGGCAGCTGA    240
GCTGATTGCC AACTCACTGG CCACTGCAGG GGATGGCCTG ATCGAGCTGC GCAAGCTGGA    300
AGCTGCAGAG GACATCGCGT ACCAGCTCTC ACGCTCTCGG AACATCACCT ACCTGCCAGC    360
GGGGCAGTCC GTGCTCCTCC AGCTGCCCCA GTGAGGGCCC ACCCTGCCTG CACCTCCGCG    420
GGCTGACTGG GCCACAGCCC CGATGATTCT TAACACAGCC TTCCTTCTGC TCCCACCCCA    480
GAAATCACTG TGAAATTTCA TGATTGGCTT AAAGTGAAGG AAATAAAGGT AAAATCACTT    540
CAGATCTCTA ATTAGTCTAT CAAATGAAAC TCTTTCATTC TTCTCACATC CATCTACTTT    600
TTTATCCACC TCCCTACCAA AAATTGCCAA GTGCCTATGC AAACCAGCTT TAGGTCCCAA    660
TTCGGGGCCT GCTGGAGTTC CGGCCTGGGC ACCAGCATTT GGCAGCACGC AGGCGGGGCA    720
GTATGTGATG GACTGGGGAG CACAGGTGTC TGCCTAGATC CACGTGTGGC CTCCGTCCTG    780
TCACTGATGG AAGGTTTGCG GATGAGGGCA TGTGCGGCTG AACTGAGAAG GCAGGCCTCC    840
GTCTTCCCAG CGGTTCCTGT GCAGATGCTG CTGAAGAGAG GTGCCGGGGA GGGGCAGAGA    900
GGAAGTGGTC TGTCTGTTAC CATAAGTCTG ATTCTCTTTA ACTGTGTGAC CAGCGGAAAC    960
AGGTGTGTGT GAACTGGGCA CAGATTGAAG AATCTGCCCC TGTTGAGGTG GGTGGGCCTG   1020
ACTGTTGCCC CCCAGGGTCC TAAAACTTGG ATGGACTTGT ATAGTGAGAG AGGAGGCCTG   1080
GACCGAGATG TGAGTCCTGT TGAAGACTTC CTCTCTACCC CCCACCTTGG TCCCTCTCAG   1140
ATACCCAGTG GAATTCCAAC TTGAAGGATT GCATCCTGCT GGGGCTGAAC ATGCCTGCCA   1200
AAGACGTGTC CGACCTACGT TCCTGGCCCC CTCGTTCAGA GACTGCCCTT CTCACGGGCT   1260
CTATGCCTGC ACTGGGAAGG AAACAAATGT GTATAAACTG CTGTCAATAA ATGACACCCA   1320
GACCTTCC                                                           1328
```

(2) INFORMATION FOR SEQ ID NO:23:

```
    (i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA primer"

(xi) SEQUENCE DESCRIPTION: SEQ ID NO:23:

AAGGTGGCTT TCTGGTGAAG                                                       20

(2) INFORMATION FOR SEQ ID NO:24:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA primer"

(xi) SEQUENCE DESCRIPTION: SEQ ID NO:24:

GGCCTCCGTC CTGTCACTG                                                        19

(2) INFORMATION FOR SEQ ID NO:25:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA primer"

(xi) SEQUENCE DESCRIPTION: SEQ ID NO:25:

CTTTGGCAGG CATGTTCAGC                                                       20
```